(12) United States Patent
Sueppel et al.

(10) Patent No.: US 6,697,655 B2
(45) Date of Patent: Feb. 24, 2004

(54) LOW POWER PULSE OXIMETER

(75) Inventors: Brian E. Sueppel, Grafton, WI (US); David W. Mortara, River Hills, WI (US)

(73) Assignee: Mortara Instrument, Inc., Milwaukee, WI (US)

( * ) Notice: Subject to any disclaimer, the term of this patent is extended or adjusted under 35 U.S.C. 154(b) by 0 days.

(21) Appl. No.: 09/972,077

(22) Filed: Oct. 5, 2001

(65) Prior Publication Data

US 2003/0069486 A1 Apr. 10, 2003

(51) Int. Cl.[7] .................................................. A61B 5/00
(52) U.S. Cl. ....................... 600/322; 600/310; 600/323
(58) Field of Search ................................ 600/310, 322, 600/323; 340/573.1; 607/16, 22

(56) References Cited

U.S. PATENT DOCUMENTS

| | | | | |
|---|---|---|---|---|
| 4,750,495 A | * | 6/1988 | Moore et al. ................. | 607/22 |
| 5,924,979 A | * | 7/1999 | Swedlow et al. ............ | 600/323 |
| 6,363,280 B1 | * | 3/2002 | Mouchawar et al. .......... | 607/16 |
| 2003/0028085 A1 | * | 2/2003 | Ammar ....................... | 600/323 |

* cited by examiner

Primary Examiner—Charles Marmor
Assistant Examiner—David J. McCrosky
(74) Attorney, Agent, or Firm—Patterson, Thuente, Skaar & Christensen, P.A.

(57) ABSTRACT

A low power pulse oximeter includes an input stage for amplifying a signal received from a light detector that is switchably connected to the power supply that powers the amplifier. The oximeter also includes an output stage with an LED driver circuit that is switchably connected to the power supply that powers the LED driver circuit. The input and output stages are switchably connected to the power supply when measurements need to be taken. When measurements do not need to be taken, they are switched off to reduce the power consumption of the oximeter.

22 Claims, 4 Drawing Sheets

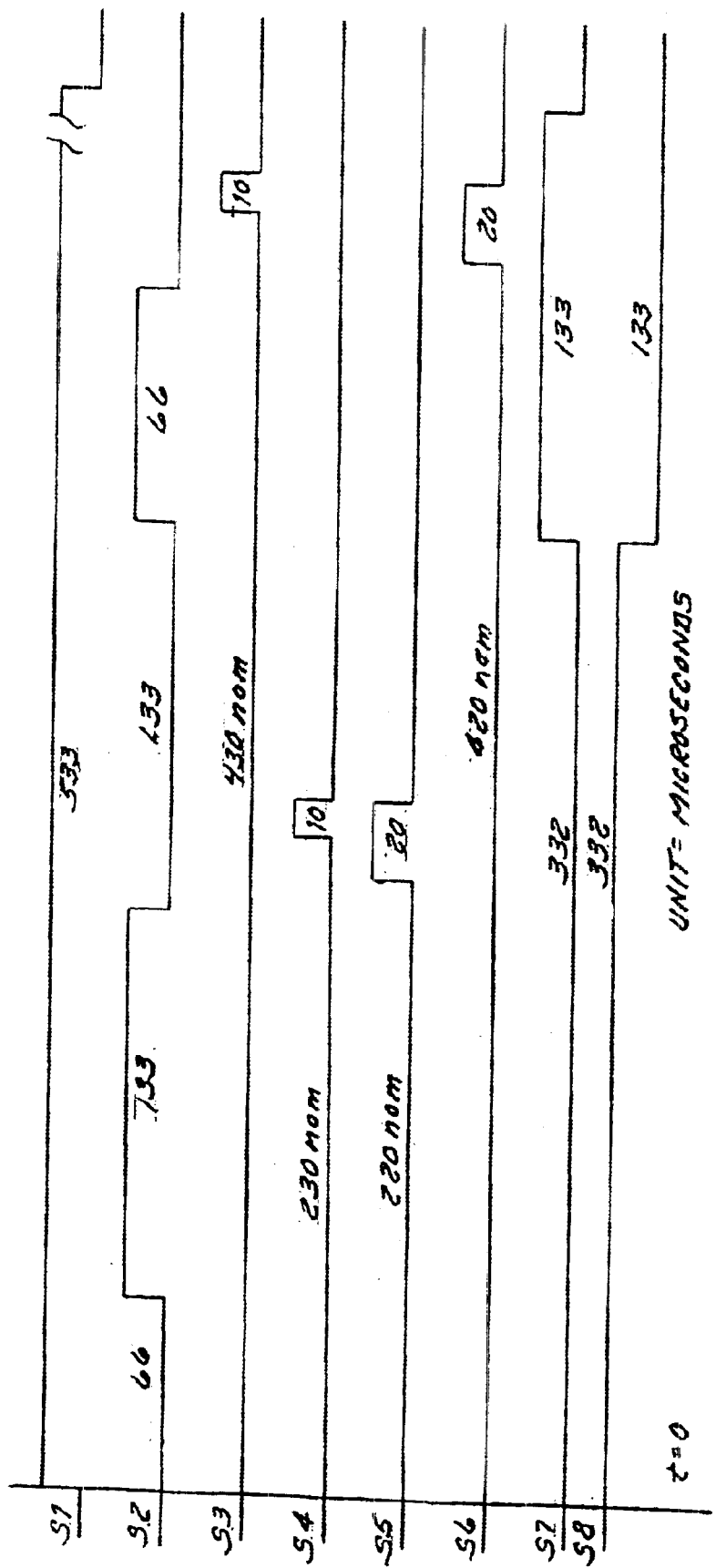

LOW POWER PULSE OXIMETER

FIELD OF THE INVENTION

The invention relates to pulse oximeters. More particularly, it relates to methods for reducing power consumption in pulse oximeters by selectively disabling circuitry used to monitor blood oxygenation.

BACKGROUND OF THE INVENTION

Pulse oximetry refers to a process for determining the oxygenation level of the blood in a patient's blood stream. It is particularly useful when monitoring persons with chronic pulmonary blockages and patient undergoing surgery.

One problem with pulse oximeters is their high power consumption. The front-ends of pulse oximeters use high power consumption devices such as LED's and amplifiers to generate light and amplify that light after it passes through perfused tissue. Several times per second, pulse oximeters generate individual pulses of light that are transmitted through perfused tissue. These pulses are then received by a photodetector (typically a photodiode) and the amount of light of at least two different wavelengths is received. These individual pulses of light are then separately a serially processed to determine the degree to which the blood is perfused. The light intensity is digitized in analog to digital converters and is numerically manipulated to indicate the degree (typically the percentage) of oxygenation.

Blood oxygenation does not change instantaneously from pulse to pulse. Any change in oxygenation is a gradual process. Yet generating the pulses and calculating the corresponding oxygenation level happen virtually instantaneously. Thus, there is a significant amount of time in which pulses are not generated and processed. In typically oximeters, the circuitry that processes the pulses is powered up all the time, however. As a result, the circuits consume much more power than is needed. In the relatively long intervals between actual pulse generation and pulse measurement, the circuitry consumes power. This unnecessary power consumption can rapidly drain a battery powered oximeter and require the operator to either plug the oximeter into an AC supply that constantly trickle-charges the battery. This defeats the purpose of having a battery itself. Alternatively, the oximeter must be monitored regularly to insure it does not fail due to an exhausted battery. This defeats the purpose of having a monitoring device.

Not all components of a pulse oximeter can or should be shut down between pulse measurements, however. For example, the display that indicates the oxygenation levels should indicate the current oxygenation level at all times. Second, the microcomputer circuitry that keeps track of oxygenation trends should not be powered down, since this would typically reset its memory and cause it to "forget" the previous oxygenation history.

It is an object of this invention to provide a method and apparatus for selectively de-powering the light generating and amplifying circuits of a pulse oximeter between actual pulse measurements. It is also an object of this invention to provide a method and apparatus for de-powering the light receiving and amplifying circuits of a pulse oximeter between actual pulse measurements.

SUMMARY OF THE INVENTION

In accordance with a first embodiment of the invention, a low power pulse oximeter is provided having a sensor further comprising a source of light configured to generate pulses of light in at least two wavelengths of light and a photodetector configured to receive the pulses of light and to generate an analog electrical signal indicative of the amplitude of light in each of the pulses, at least one amplifier that is coupled to the photodetector to amplify the analog electrical signal, a power supply that is coupled to the at least one amplifier to provide power to the at least one amplifier, an analog to digital converter that is coupled to the amplifier to receive and convert the amplified analog electrical signal into a digital signal, a microcomputer configured to receive the digital signal and to calculate a blood oxygenation level therefrom, and a switch disposed between the at least one amplifier and the power supply to selectively interrupt a flow of amplifier power from the power supply to the at least one amplifier.

In accordance with a second embodiment of the invention, a low power pulse oximeter for driving and monitoring an oximeter sensor is provided, wherein the sensor includes at least two LED's configured to generate pulses of light at two different wavelengths and at least one photodetector responsive to the two wavelengths of light, the oximeter including a power supply configured to provide electrical power, a switch coupled to the power supply to selectively enable and disable a flow of the electrical power from the power supply between successive pulses of light thereby reducing power consumption, a preamplifier stage configured to be coupled to the at least one photodetector to receive an electrical signal from the photodetector representative of an amount of light impinging on the photodetector and to amplify that electrical signal, wherein the preamplifier stage is coupled to the switch to receive the flow of electrical power, an analog to digital converter stage coupled to the preamplifier stage to convert the amplified signal to a corresponding digital representation, and a microcomputer coupled to the analog-to-digital converter stage to receive the digital representation and calculate an oxygen saturation.

In accordance with a third embodiment of the invention, a method is provided for reducing the power consumption of a pulse oximeter having a photodetector for detecting pulsatile variations in light transmission through perfused tissue, a preamplifier stage to amplify electrical analogues of the pulsatile variations indicative of an oxygen perfusion, an analog to digital converter for converting an output of the preamplifier into a corresponding digital representation of the output, and a microprocessor configured to convert the digital representation to a value indicative of an oxygen perfusion, the method including the steps of: (a) generating a pulse of infrared light; (b) converting at least a portion of the pulse of infrared light into an infrared electrical signal; (c) energizing the preamplifier stage; (d) amplifying at least a portion of the infrared electrical signal in the preamplifier stage; (e) transmitting the amplified infrared signal to the analog to digital converter; (f) deenergizing the preamplifier stage; (g) generating a pulse of red light; (h) converting at least a portion of the pulse of red light into an red electrical signal; (i) reenergizing the preamplifier stage; (j) amplifying at least a portion of the infrared electrical signal in the preamplifier stage; (k) transmitting the amplified infrared signal to the analog to digital converter; and (l) deenergizing the preamplifier stage.

In accordance with a fourth embodiment of the invention, a low-power pulse oximeter is provided, including a microcomputer configured to generate a digital signal indicative of a desired amount of light, a digital to analog converter coupled to the microcomputer to convert the digital signal into an analog signal indicative of a desired amount of light, at least one amplifier coupled to the digital to analog converter to amplify the analog signal to an amplitude sufficient to generate the desired amount of light, a power supply coupled to the at least one amplifier to provide power to the at least one amplifier, a switch disposed between the power supply and the at least one amplifier to selectively interrupt a flow of amplifier power from the power supply to the at least one amplifier, and a light source coupled to the at least one amplifier and configured to generate the desired amount of light upon receipt of the amplified analog signal.

In accordance with a fifth embodiment of the invention, a medical monitoring system is provided, including a sensor configured to sense a physical parameter of a patient and to generate a sensor signal, at least one amplifier that is coupled to the sensor to amplify the sensor signal, a battery that is coupled to the at least one amplifier to provide power to the at least one amplifier, an analog to digital converter that is coupled to the amplifier to receive and convert the amplified signal to a digital signal, a microcomputer configured to receive the digital signal and to calculate a value indicative of the physical parameter therefrom, and a switching circuit disposed between the at least one amplifier and the battery to selectively interrupt a flow of electrical power from the battery to the at least one amplifier.

BRIEF DESCRIPTION OF THE DRAWINGS

The present invention will become more fully understood from the following detailed description, taken in conjunction with the accompanying drawings, wherein like reference numerals refer to like parts, in which:

FIG. 4 illustrates a timing diagram of the system of FIG. 1 using the alternative circuitry of FIGS. 2 and 3.

DETAILED DESCRIPTION OF THE PREFERRED EMBODIMENTS

Figure 1:
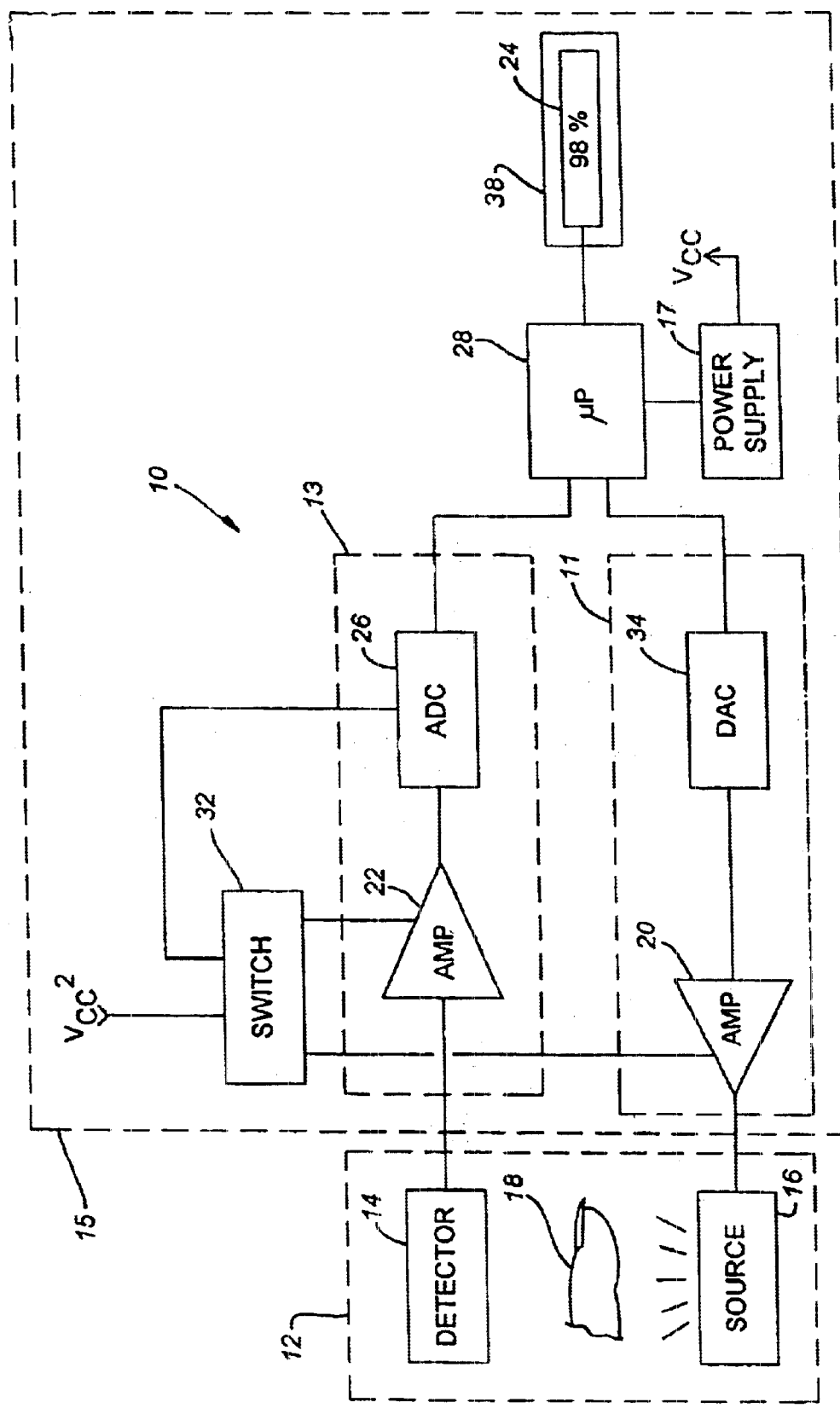
FIG. 1 is an overall schematic representation of a first embodiment of the system illustrating a microcomputer circuit coupled to an input stage and output stage, a sensor coupled to the input and output stages, and a switching circuit for controlling the power consumption of the sensor, the input stage and the output stage.

Referring to FIG. 1, a pulse oximeter 10 is shown including a sensor 12 having a light detector 14 and a light source 16 that together transmit light through perfused tissue 18 (here shown as a finger). Sensor 12 is coupled to an output stage 11 that drives the light source, and an input stage 13 that receives light from the light detector and converts it into digital form.

Oximeter 10 also includes a microcomputer circuit 28 that is coupled to the input and output stages and controls the input and output stages to energize the light source and to read the signals generated by the light detector and convert them to digital form for later processing, and to calculate a digital value indicative of the perfusion of tissue 18 based at least in part on the converted signals.

The microcomputer circuit may include a microprocessor or a microcontroller or alternatively a state logic device. It may be implemented using a single integrated circuit device or alternatively using a plurality of devices in communications with one another by data lines (either serial or parallel), address and/or control lines to transmit data and control information between the devices and the other components of the system.

Oximeter 10 further includes an electronic display 30 that is coupled to the microcomputer to receive the value indicative of the perfusion of tissue 18 and to display a numerical value indicative of the degree of perfusion.

Oximeter 10 is disposed in a housing 15 and includes an electrical power source (or "power supply") 17, here shown in a preferred embodiment as a battery that is also disposed inside housing 15. The battery generates power for all the various components of the oximeter, including, without limitation, the input and output stages and the microcomputer circuit. "Vcc" indicates this power, and the implied connection to battery 17 in the FIGURES and the description. When using a battery as a power source, the present invention and its inherent reduced power consumption provides for extended system usage between battery recharging and thus is particularly beneficial by reducing recharging down time.

In addition to the foregoing components, oximeter 10 also includes a switching circuit 32 which is provided to control the power consumption of the input stage and/or the output stage by switching the input and output stages from a high power consumption mode to a lower power consumption mode. Switching circuit 32 is preferably coupled to the input and output stages to regulate their power consumption by reducing or eliminating the power consumed by one or more of their components. More preferably switching circuit 32 is configured to connect and disconnect the power source (Vcc) from one or more components of the input stage and/or output stage. Even more preferably it is coupled to and driven by microcomputer circuit 28, which is configured to control the switching circuit to connect and disconnect the power source to the one or more components of the input stage and/or output stage.

Light source 16 is configured to generate light in both the infrared and red bands. It may include separate light-emitting elements, each configured to generate light in a different band (or at a different frequency), or a single light-emitting element configured to generate light in a plurality of bands (or at a plurality of frequencies).

Light detector 14 has a detecting surface responsive to light in both the red and infrared bands and converts that light into an electrical signal indicative of the amplitude of light incident on the detecting surface. It may include a single detecting surface responsive to light in a plurality of bands or frequencies, or a plurality of surfaces, each surface responsive to a different band or frequency.

Input stage 13 includes a detector amplifier circuit 22 and an ADC circuit 26. Detector amplifier circuit 22 is coupled to light detector 14 to receive and amplify detector electrical signals indicative of the amount of light received by light detector 14. ADC 26 is coupled to detector amplifier circuit 22 to receive and to convert the amplified electrical signals into digital form. ADC circuit 26 is also coupled to microcomputer circuit 28 to provide the microcomputer circuit with the converted digital signal. Microcomputer circuit 28 is configured to control ADC circuit 26, signaling it when to convert an analog signal into a corresponding digital value. ADC circuit 26 preferably includes an ADC integrated circuit. ADC circuit 26 may also include a sample-and-hold (S/H) circuit configured to sample the amplified signal and save it while the analog-to-digital conversion is being performed. This S/H circuit may be formed integrally with the ADC integrated circuit or may be formed of additional components, such as a capacitor in which the signal may be temporarily saved and a switching circuit to connect the S/H circuit to the detector amplifier circuit. The ADC integrated circuit is preferably a single channel ADC configured to convert both red and infrared signals to red and infrared digital values, respectively. More preferably, it is a multi-channel ADC having one channel dedicated to the conversion of one band or frequency of light, and a second channel dedicated to the conversion of a second band or frequency of light. The multiple channels may include a first channel responsive to a first band or frequency in the red band of light and a second channel responsive to a second band or frequency in the infrared band of light.

Output stage 11 includes a source amplifier (or "driver") circuit 20 and a digital-to-analog converter (DAC) circuit 34. DAC circuit 34 is coupled to and controlled by microcomputer 28 to receive a digital value indicative of a desired magnitude of light to be emitted by light source 16. DAC 34 receives this value, and converts it to an equivalent analog signal at the command of microcomputer circuit 28. DAC 34 may be a single- or a multi-channel DAC. DAC 34 may include at least one integrated circuit digital-to-analog converter chip. Source amplifier circuit 20 is coupled to DAC 34 to receive the DAC-converted signal and to drive light source 16 to emit the desired magnitude of light an electronic display 30 that is coupled to the microcomputer to receive the value indicative of the degree of perfusion and to display a numerical value indicative of the degree of perfusion.

Source and detector amplifier circuits 20 and 22 may include analog integrated circuit amplifiers to amplify their respective signals. Analog-to-digital converter circuit 26 may be a single channel ADC configured to convert both red and infrared signals to red and infrared digital values, respectively, or it may be a multi-channel ADC having one channel dedicated to the conversion of one band or frequency of light, and a second channel dedicated to the conversion of a second band or frequency of light. The multiple channels may include a first channel responsive to a first band or frequency in the red band of light and a second channel responsive to a second band or frequency in the infrared band of light. Analog-to-digital converter circuit 26 may also include a DC offset circuit that generates an offsetting DC signal to shift the digitized values into a preferred range of values.

In operation, microcomputer circuit 28 transmits a digital value to DAC 34 that is indicative of a desired magnitude of red light to be generated by light source 16. DAC 34 converts this digital value into a corresponding analog signal. Microcomputer circuit 28 also signals switching circuit 32 to turn on (i.e. apply power to) source amplifier circuit 20 and detector amplifier circuit 22. Source amplifier circuit 20 then drives light source 16, which generates light in either the red or infrared wavelength bands. This light passes through perfused tissue 18 and is received at light detector 14. Light detector 14 generates a signal indicative of the magnitude of light impinging on it and provides this signal to detector amplifier circuit 22. Detector amplifier circuit 22 receives this signal and amplifies it. The amplified signal is provided to ADC 26. Microcomputer circuit 28 signals ADC 26 to convert the amplified signal into digital form. When this conversion is done, microcomputer circuit 28 is configured to receive the digitized value signal from ADC 26 and to save it for later processing. Once the signal has been received and converted, or (in the case of an oximeter employing a sample-and-hold circuit) has been sampled and saved, microcomputer 28 is configured to signal switching circuit 32 to turn off the power applied to source amplifier circuit 20 and detector amplifier circuit 22.

The paragraph above describes how the oximeter generates a red light pulse, transmits it through the perfused tissue, receives the transmitted light and converts it into a digital value for processing. Oximeters, however, require values indicative of both transmitted red and transmitted infrared light in order to calculate oxygen perfusion. For this reason, the oximeter is configured to repeat the above process for a pulse of infrared light. Instead of sending a value indicative of a desired magnitude of red light to DAC 34 during this repetition, microcomputer circuit 28 sends a value indicative of a desired magnitude of infrared light. In other respects the process is the same for the infrared light pulse as it is for the red light pulse.

By providing a switching circuit 32 that connects and disconnects components in the input and output stages from power after each measurement is made, the power consumption of the input and output stages is significantly reduced.

Microcomputer circuit 28 is configured to repeat this process of gathering red and infrared transmitted light values at a rate of around 120 Hz. Microcomputer circuit 28 is also configured to periodically determine the actual oxygen perfusion from these values (in a conventional fashion) approximately once every second. The actual process by which the oxygen perfusion is calculated from the red and infrared transmitted light values forms no part of this invention, and is well known to those of ordinary skill in the art.

Figure 2:
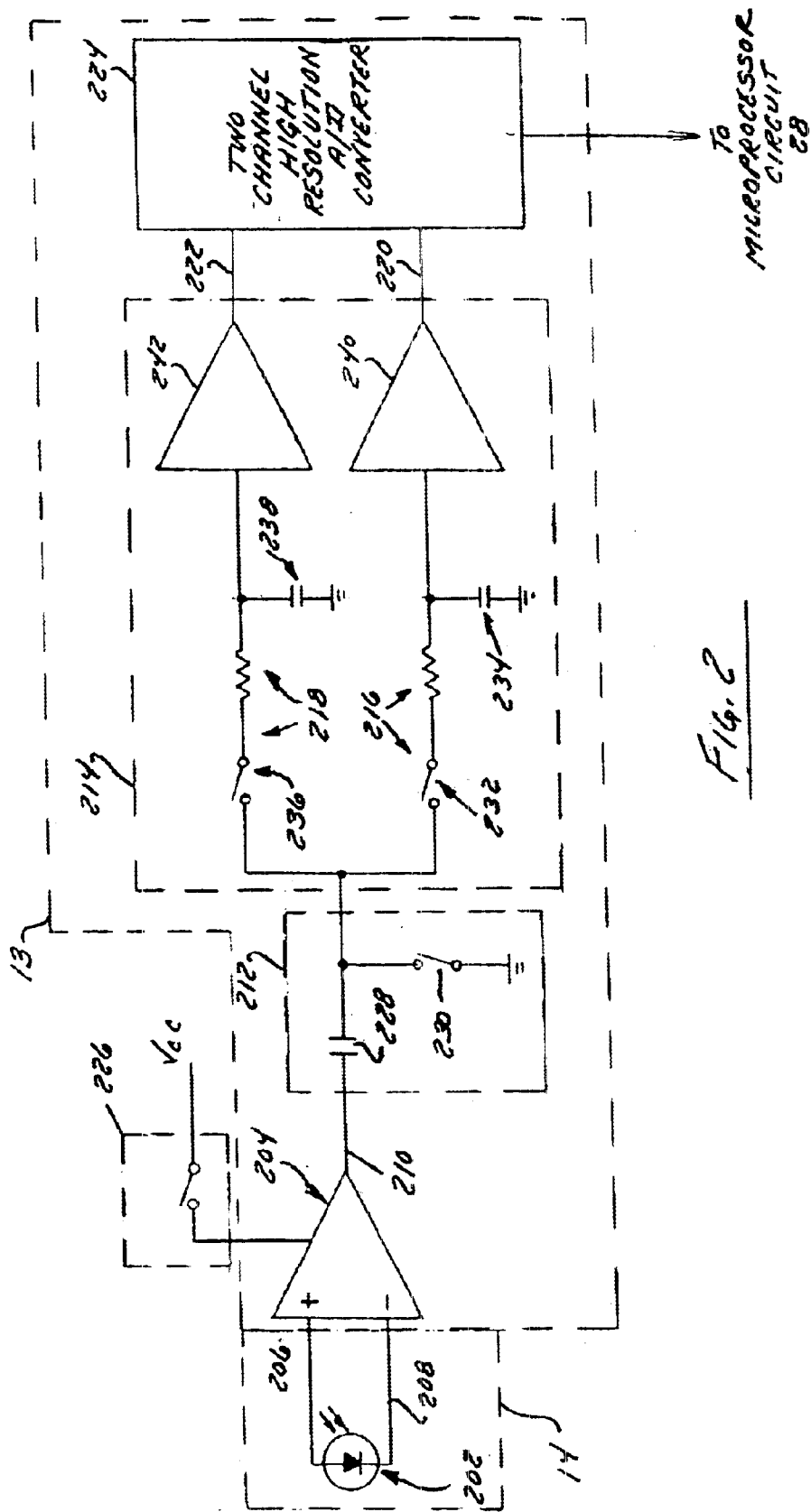
FIG. 2 illustrates a second embodiment of the input stage showing an alternative sensor, and alternative sensor amplifier circuit, an alternative sample-and-hold circuit, and alternative switching circuit and an alternative ADC.

Referring now to FIG. 2, second embodiments of the input stage 13 and light detector 14 are shown. The operation and capabilities of these alternative embodiments are similar to the embodiment of FIG. 1. In the embodiments of FIG. 2, the light detector is a photodiode 202 that is coupled to an input amplifier circuit 204. Photodiode 202 has a detecting surface responsive to light in both the red and infrared bands. It converts that light into an electrical signal indicative of the amplitude of light incident on the detecting surface. The input amplifier circuit is configured to receive and amplify photodiode 202 signals indicative of the amount of light received by the photodiode and, in particular, to amplify the difference between the signals on the photodiode's two input leads 206 and 208. By amplifying this difference the input amplifier 202 reduces common-mode noise. The amplified signal is provided on signal line 210, which is coupled to and transmits the amplified signal to dark level removal circuit 212.

Dark level removal circuit 212 removes that portion of the signal caused by interfering light such as ambient light from nearby light fixtures. Ambient light leakage adds to the light that is transmitted through the perfused tissue and, if not compensated for, contributes to perfusion calculation errors. Once the light leakage is compensated for in the dark level removal circuit, the signal is transmitted to a sample-and-hold (S/H) circuit 214.

Sample-and-hold circuit 214 takes a sample of the signal from input amplifier 204 and saves it temporarily so the signal can be converted into digital form. The S/H circuit 214 includes two separate sub-circuits, a red light sub-circuit 216 and an infrared light circuit 218. Red light sub-circuit 216 samples a signal that represents a quantity of red light passing through perfused tissue and falling on photodiode 202. Infrared light sub-circuit 218 samples a signal the represents a quantity of infrared light falling on photodiode 202.

Each sub-circuit outputs its signal on a separate signal line. Signal line 220 carries the red signal and signal line 222 carries the infrared signal. These two signal lines, in turn, are coupled to separate channels of an analog-to digital converter (ADC) 224.

ADC 224 has two analog input channels; one channel for converting the red signal into digital form, and one channel for converting the infrared signal into digital form. The digital output of ADC 224 is coupled to microcomputer circuit 28 (not shown).

Input amplifier circuit 204 can be switched into a quiescent or "off" state and back into an active or "on" state by switching circuit 226. In a preferred embodiment, switching circuit 226 (represented schematically in FIG. 2 as a simple single pole switch) is coupled to amplifier circuit 204 to connect and disconnect a source of electrical power (Vcc) to amplifier circuit 204. Switching circuit 226 is coupled to and controlled by microcomputer circuit 28. Microcomputer circuit 28 can thereby reduce the power consumed by input amplifier circuit 204.

Dark level removal circuit 212 includes a capacitor 228 that stores the dark level component of the signal generated by amplifier circuit 204. When light source 16 is turned off, microcomputer circuit 28 closes switch 230, which grounds the output side of capacitor 228. The dark level signal is present on the input side (signal line 210) capacitor 210. Once capacitor 228 is charged to the dark level, microcomputer circuit 28 opens switch 230, thereby capturing the dark level charge on capacitor 228.

After the dark level is captured on capacitor 228, the light source (see FIG. 1 or FIG. 3) is turned on and a new combined signal equivalent to the leakage light (i.e. the dark level) plus the light transmitted through the perfused tissue is transmitted to capacitor 228. Since the dark level is already stored on capacitor 228, however, it is removed from the combined signal and only the actual signal indicative of the light passing through the perfused tissue is transmitted forward to S/H circuit 214. In this manner, the system reduces the dark level and the effects of light leakage.

S/H circuit 214 is coupled to the dark removal circuit 212. It samples the signal and presents it to ADC 224 for digital conversion. It has two circuit paths, one for red light 216 and one for infrared light 218. It also includes two switch circuits 232 and 236 that selectively couple the red and infrared sub-circuits to the dark level removal circuit. Switching circuit 232 (shown symbolically in FIG. 2 as a simple single pole switch) connects a charge capacitor 234 to the dark removal circuit to be charged. Switching circuit 236 (shown symbolically in FIG. 2 as a simple single pole switch) connects a charge capacitor 238 to the dark removal circuit to be charged. Switching circuits 232 and 236 are coupled to and controlled by microcomputer circuit 28. Microcomputer circuit 28 is configured to close switching circuit 232 when photodiode 202 receives red light, thereby permitting capacitor 234 to charge to a level indicative of the red light transmitted through the perfused tissue. Microcomputer circuit 28 is configured to close switching circuit 236 when photodiode 202 receives infrared light, thereby permitting capacitor 238 to charge to a level indicative of the infrared light transmitted through the perfused tissue. In this manner, microcomputer circuit 28 and S/H circuit 214 are configured to provide an analog signal indicative of the red light transmitted through the perfused tissue on signal line 22 and to provide an analog signal representative of the infrared light transmitted through the perfused tissue on signal line 222. S/H circuit 214 also includes two high-impedance driver circuits 240 and 242 that drive the red and infrared analog signals before providing them to ADC 224 on signal lines 220 and 222, respectively. These drivers insure that the process of converting the signals will not significantly reduce the charge stored on capacitors 234 and 238 during conversion of the charge (i.e. the analog signal) into digital form.

Figure 3:
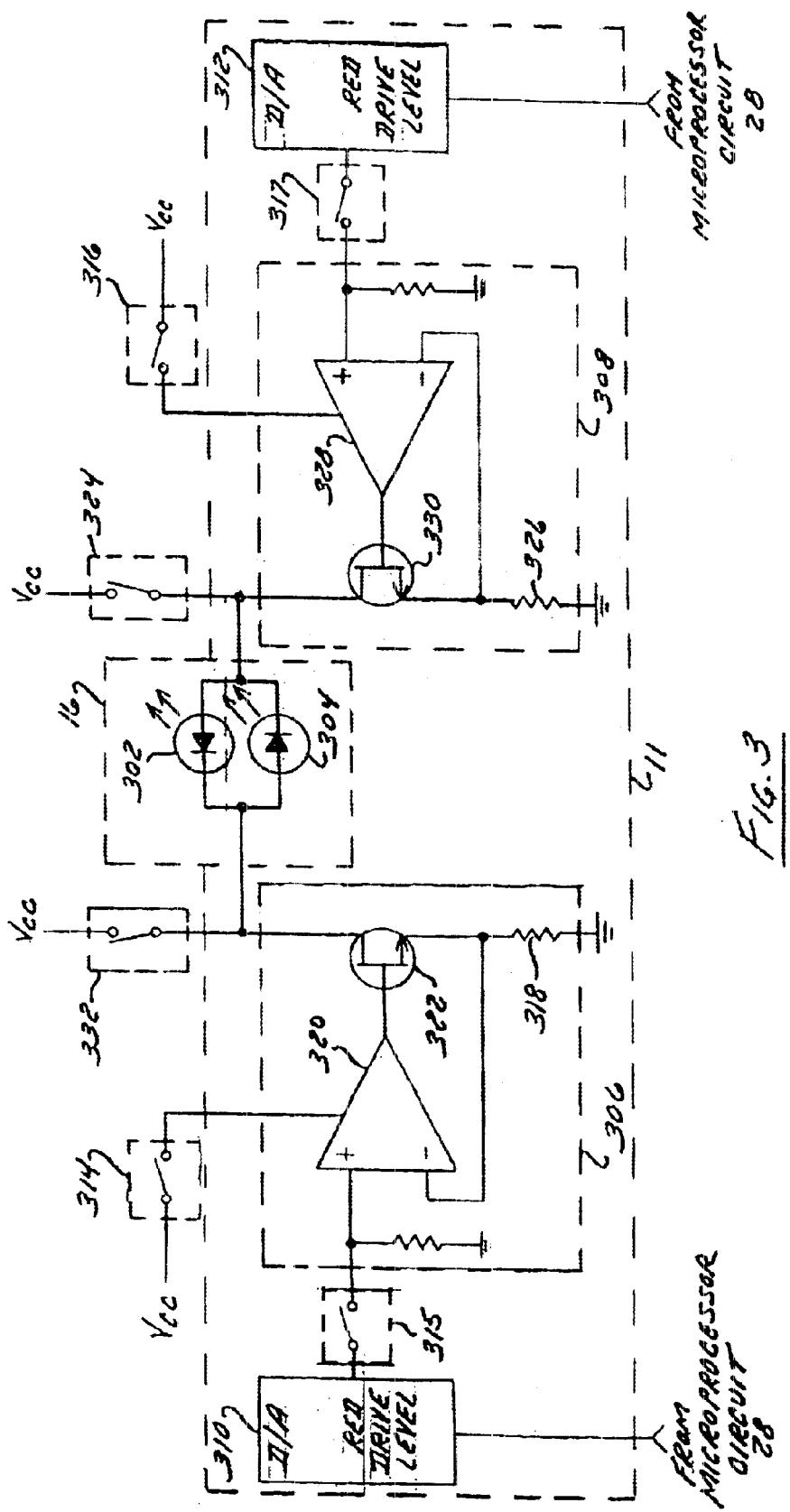
FIG. 3 illustrates a second embodiment of the output stage showing an alternative sensor circuit, an alternative digital-to-analog (DAC) circuit, and an alternative source driver circuit (e.g. the LED amplifier circuit.

Referring now to FIG. 3, alternative embodiments of light source 16, switching circuit 32 and output stage 11 of FIG. 1 are shown. The operation and capabilities of these embodiments are similar to the embodiment of FIG. 1. In these alternative embodiments, two light-emitting diodes (LED's) 302 and 304 are shown as alternatives for light source 16 of FIG. 1. The two LED's are coupled to and driven by LED amplifier (or driver) circuits 306 and 308, which are alternatives for source amplifier circuit 20 of FIG. 1. Amplifier circuits 306 and 308, in turn, are coupled to DACS 310 and 312 which are alternatives to DAC circuit 34 of FIG. 1. Switching circuits 314 and 316 are shown as alternative embodiments of switching circuit 32 of FIG. 1. They are coupled to amplifier circuits 306 and 308, respectively, to control the flow of power (Vcc) to the LED amplifier circuits 306 and 308, respectively. Switching circuits 315 and 317 are coupled between DAC's 310 and 312 and LED amplifier circuits 306 and 308, respectively, to connect the DAC's to and disconnect the DAC's from their respective LED amplifier circuits.

In operation, microcomputer circuit 28 is coupled to and drives the DAC's with digital values indicative of a desired LED light magnitude. The DAC's turn these digital values into analog signals that are also indicative of a desired LED light magnitude. The analog signals from the DAC's are then amplified in LED amplifier circuits 306 and 308, and are then applied to the LED's themselves, thereby generating the desired light amplitude.

The LED's are connected back-to-back, anode to cathode, to emit light when current flows in both directions. When current flows in one direction, one LED emits light. When current flows in the other direction, the other LED emits light. One LED amplifier circuit controls the flow of current in one direction, and the other LED amplifier circuit controls the flow of current in the other direction.

The two LED amplifier circuits are substantially the same and are arranged in back-to-back fashion in the circuit as shown in FIG. 3.

When circuit 306 receives a voltage signal from DAC 310, it controls current flow through red LED 302 until the voltage across sense resistor 318 is the same as the voltage generated by the DAC. The voltage across sense resistor 318 is proportional to the current through red LED 302, and the current through red LED 302 is substantially proportional to the light emitted by red LED 302. Operational amplifier 320 is configured to operate as a current source and generates a current that is applied to transistor 322. Transistor 322, in turn, throttles the flow of current from the voltage source (Vcc) through switching circuit 324, through red LED 302, through transistor 322 and through sense resistor 318 to ground. As the current flow increases though this circuit, the voltage rises across sense resistor 318 until it equals the voltage generated by DAC 310. When these two voltages approach equality, their difference approaches zero and the output of the operational amplifier stabilizes. This, in turn stops the current through transistor 322 from increasing, and hence maintains the current flow through transistor 322 substantially constant. In short, the current flow through red LED 302 is maintained substantially proportional to the voltage signal generated by DAC 310. When this voltage signal changes, the current through the red LED changes accordingly.

When circuit 308 receives a voltage signal from DAC 312, it controls current flow through infrared LED 304 until the voltage across sense resistor 326 is the same as the voltage generated by the DAC. The voltage across sense resistor 326 is proportional to the current through infrared LED 304, and the current through infrared LED 304 is substantially proportional to the light emitted by infrared LED 304. Operational amplifier 328 is configured to operate as a current source and generates a current that is applied to transistor 330. Transistor 330, in turn, throttles the flow of current from the voltage source (Vcc) through switching circuit 332, through infrared LED 304, through transistor 330 and through sense resistor 326 to ground. As the current flow increases though this circuit, the voltage rises across sense resistor 326 until it equals the voltage generated by DAC 312. When these two voltages approach equality, their difference approaches zero and the output of the operational amplifier stabilizes. This, in turn stops the current through transistor 330 from increasing, and hence maintains the current flow through transistor 330 substantially constant. In short, the current flow through the infrared LED is maintained substantially proportional to the voltage signal generated by DAC 312. When this voltage signal changes, the current through infrared LED 304 changes accordingly.

The power consumption of LED amplifier 306 can be significantly reduced by operation of switching circuits 324 and 314. The power consumption of LED amplifier 308 can be significantly reduced by operation of switching circuits 332 and 316. These switching circuits selectively control the power consumed by amplifiers 306 and 308 (and more particularly to operational amplifiers 320 and 328) by disconnecting them from the power supply (Vcc). While the amplifiers used here are de-powered by disconnecting them from their source of operating power, the switching circuits 314 and 316 may also be configured to place the amplifiers in a low power or stand-by mode of operation in which they are quiescent.

As recited above, microcomputer circuit 28 is configured to determine the oxygenation or perfusion of tissue 18 in a conventional fashion. It is also configured, however, to selectively control each of switching circuits 226, 230, 232, 236, 314, 315, 316, 317, 324 and 332 in the repetitive pattern described below in order to gather signals indicative of the red and infrared light transmitted through the perfused tissue.

FIG. 4 is a timing diagram indicating the sequence of actions taken by the microcomputer circuit 28 when it controls the various switching circuits described above. The scale begins at time t=0 and continues from left to right until the end if an entire measurement cycle at t=8330 microseconds. The cycle is preferably repeated every 8330 microseconds (i.e. at a rate of 120 Hz) while the oximeter is operating. More preferably, it is repeated at a rate of at least 60 Hz.

In FIG. 2, S1 refers to switching circuits 226, 314 and 316. S2 refers to switching circuit 230. S3 refers to switching circuit 236. S4 refers to switching circuit 232. S5 refers to switching circuit 315. S6 refers to switching circuit 317. S7 refers to switching circuit 332 and S8 refers to switching circuit 324.

At time t=0, microcomputer circuit 28 closes switching circuits 226, 314, and 316. All the other switching circuits are open except switching circuit 324 which was opened prior to time t=0. Even though switching circuit 324 is closed, however, no current flows through red LED 302, since switching circuit 314 is open and hence transistor 322 is shut off.

When closed at time t=0, the three switching circuits 226, 314, and 316, begin supplying power to amplifier circuits 204, 306 and 308. Power is applied to these circuits for a period sufficient for them to stabilize in their proper operational modes, preferably about 66 microseconds. This time interval may vary depending upon the type of amplifiers used.

At time t=66 microseconds, the amplifier circuits have stabilized. Microcomputer circuit 28 then sets the dark level by closing switching circuit 230. Since neither LED has been turned on yet, the closing of switch 230 will charge capacitor 228 to the magnitude of the ambient light noise (the dark level).

Once switch 230 is closed, it is held closed for a time sufficient to charge capacitor 230 to the dark level or preferably about 133 microseconds until time t=200. This time interval may vary depending upon the size and type of capacitor 230 used. At time t=200, microcomputer circuit 28 opens switching circuit 230 to hold the dark level charge on the input side of capacitor 230.

At time t=220 microseconds, microcomputer circuit 28 closes switching circuit 315 connecting the output of DAC 310 to LED amplifier 306. Sometime prior to t=220 microseconds, microcomputer circuit 28 preferably signaled DAC 310 to generate an analog signal indicative of the desired magnitude of red LED light. Approximately 10 microseconds later, once the signal from amplifier 306 has stabilized, microcomputer circuit 28 then closes switching circuit 314 to thereby apply power to LED amplifier 306. LED amplifier circuit 306 the drives red LED 302 until it generates the desired amount of light.

At time t=230 microseconds, microcomputer circuit 28 closes switching circuit 232 in S/H circuit thereby charging sampling capacitor 234. Circuit 232 stays closed for approximately 10 microseconds until capacitor 234 is charged.

At time t=240 microseconds, switching circuit 232 is opened, thereby holding the charge on capacitor 234. At substantially the same time, switching circuit 315 is opened, disconnecting the signal of DAC 310 from LED amplifier 306, thereby shutting off red LED 302. Once switching circuit 232 is opened, microcomputer 28 signals ADC 224 to convert the analog red light signal stored in capacitor 234 to digital form. Once the signal is converted, microcomputer circuit 28 saves the value of the converted signal for future use in calculating the oxygen perfusion of tissue 18.

Once the digital value has been saved, microcomputer circuit 28 then proceeds to gather the infrared light value indicative of the amount of infrared light transmitted through perfused tissue 18 starting at time t=333. Since the infrared LED is to be turned on next, microcomputer circuit 28 opens switching circuit 324 and closes switching circuit 332. As in the case of the red LED, above, this does not send any current through infrared LED 304, since LED amplifier circuit 308 is still off. Both LED's are off at this point.

At substantially the same time of t=333 microseconds, microcomputer circuit 28 again compensates for the ambient light noise (the dark level) by closing switching circuit 230 and charging capacitor 228 with an amount of charge equal to the dark level.

At time t=400 microseconds microcomputer circuit 28 again opens switching circuit 230 to store the dark level charge on capacitor 228.

At time t=420 microseconds, microcomputer circuit 28 closes switching circuit 317 connecting the output of DAC 312 to LED amplifier 308. Some time prior to t=420 microseconds, microcomputer circuit 28 preferably signaled DAC 312 to generate an analog signal indicative of the desired magnitude of infrared light. Approximately 10 microseconds later, once the signal from amplifier 308 has stabilized, microcomputer circuit 28 then closes switching circuit 316 to thereby apply power to LED amplifier 308. LED amplifier circuit 306 the drives infrared LED 304 until it generates the desired amount of light.

At time t=430 microseconds, microcomputer circuit 28 closes switching circuit 236 in S/H circuit thereby charging sampling capacitor 238. Capacitor 238 is thereby charged to an analog signal value indicative of the amount of infrared light passing through perfused tissue 18. Circuit 236 stays closed for approximately 10 microseconds until capacitor 238 is charged.

At time t=440 microseconds, switching circuit 236 is opened, thereby holding the charge on capacitor 238. At substantially the same time, switching circuit 317 is opened disconnecting the signal of DAC 312 from LED amplifier 308, thereby shutting off infrared LED 304. Once switching circuit 236 is opened, microcomputer 28 signals ADC 224 to convert the analog infrared light signal stored in capacitor 238 to digital form. Once the value is converted, microcomputer circuit 28 saves the value for future use in calculating the oxygen perfusion of tissue 18.

At time t=466 microseconds, microcomputer 28 opens switching circuit 332, thus disconnecting the power supply (Vcc0 from the infrared LED. This does not shut off the infrared light, however, since the infrared light was already extinguished when switching circuit 317 was opened, disconnecting LED amplifier 308 from DAC 312 and shutting off the current flow through infrared LED 304.

Without cycling the power on and off to the LED amplifiers (drivers) 306 and 308 using the switching arrangement of FIG. 3, their power consumption is about 3.25 milliwatts apiece. By turning them off between pulses of light, their power consumption drops to about 0.25 milliwatts, or a seven-fold reduction.

By reducing the pulse time of the read and infrared LED's to approximately 20 microseconds from the industry standard 200 microseconds, the LED power consumption drops from about 2.50 milliwatts to 0.25 milliwatts. This is a 90% reduction in power consumption.

The entire cycle of measuring a transmitted red and a transmitted infrared light pulse takes perhaps 500 microseconds, total, as shown in FIG. 4. Microcomputer circuit 28 is preferably configured to repeat this cycle at a rate of at least 15 Hz. More preferably, it repeats the cycle at a rate of at least 30 Hz. Even more preferably it is configure to repeat this cycle at a rate of at least 60 Hz. Most preferably, it is configured to repeat this cycle at a rate of at least 120 Hz.

Previous oximeters that sampled red and infrared light pulses in a roughly similar fashion (but not using the novel and selective switching, powering and de-powering of circuitry described herein) used an industry standard 200-microsecond pulse width. Furthermore, they did not shut down the source and detector amplifiers between pulses, choosing instead to keep them energized at all times. As a result, the power consumption of prior art oximeters for the above portions of their circuits was on the order of 70 milliwatts. In comparison, the circuitry of the claimed device can reduce energy consumption seven-fold, to perhaps 10 milliwatts if the components and the timing are chosen with care. This seven-fold decrease in power consumption significantly extends the time a battery-powered oximeter can be used before recharging is necessary.

Thus, it can be seen that at least two alternative embodiments of an oximeter are shown in which the power consumption of an oximeter input and output stage, and in particular of amplifiers in the input and output stages can be reduced by selectively connecting and disconnecting the amplifier circuits in each stage from a power source.

While the embodiments illustrated in the FIGURES and described above are presently preferred, it should be understood that these embodiments are offered by way of example only. For example, the invention is also valuable to reduce the power of many medical monitoring systems that include a sensor that senses a physical parameter of a patient, such as the photodiode described above. In many of these devices, an amplifier stage is used to amplify the signal of a transducer or sensor such as a pressure sensor (such as one configured to be attached to the body and to measure the physical parameter of blood pressure, for example), temperature sensor (such as one configured to be attached to the body and to measure the physical parameter of body or blood temperature, for example), or an electrical sensor (such as electrodes configured to be attached to the body and to measure physical parameters such as cardiac electrical activity or brain waves). All these types of sensors among others are well-known in the art in a variety of configurations and many of those configurations couple the sensor to amplifiers that consume considerable power, which could be significantly reduced by switching power on and off to the amplifier stages that receive the raw sensor signals. Furthermore, the microcomputer circuit 28 may include programmable logic arrays (PALs or PLA's), custom gate arrays (CGA's) or other similar integrated circuits comprised of many selectively connectable semiconductor gates. These devices are well known in the art and are used to provide in operations that require fast switching with precise timing, such as the microsecond switching preferred in the embodiments herein. The invention, however, is not intended to be limited to any particular embodiment, but is intended to extend to various modifications that nevertheless fall within the scope of the appended claims.

What is claimed is:

1. A low-power pulse oximeter that comprises:
   a sensor further comprising a source of light configured to generate pulses of light at predetermined intervals in at least two wavelengths of light and a photodetector configured to receive the pulses of light and to generate an analog electrical signal indicative of the amplitude of light in each of the pulses;
   at least one amplifier that is coupled to the photodetector to amplify the analog electrical signal;
   a power supply that is coupled to the at least one amplifier to provide power to the at least one amplifier;
   an analog to digital converter that is coupled to the amplifier to receive and convert the amplified analog electrical signal to a digital signal;
   a microcomputer configured to receive the digital signal and to calculate a blood oxygenation level therefrom; and
   a switching circuit disposed between the at least one amplifier and the power supply to selectively interrupt a flow of electrical power from the power supply to the at least one amplifier;
   wherein the switching circuit is coupled to and controlled by the microcomputer and the microcomputer is configured to signal the switching circuit to interrupt the flow of amplifier power between successive pulses of light.

2. The low power pulse oximeter of claim 1, wherein the successive pulses of light include a red pulse of light and an infrared pulse of light.

3. The low-power pulse oximeter of claim 1 wherein the sensor further comprises at least one LED configured to generate light in both a red and an infrared band, and wherein the oximeter further comprises an LED amplifier circuit coupled to and configured to control the electrical current passing though the LED, and a second switching circuit coupled to the LED amplifier circuit and configured to selectively interrupt electrical power provided to the LED amplifier circuit.

4. A low power pulse oximeter for driving and monitoring an oximeter sensor, the sensor comprising at least one LED configured to generate pulses of light at two different wavelengths and at least one photodetector responsive to the two wavelengths of light, the oximeter comprising:

a power supply configured to provide electrical power;

first and second switching circuits coupled to the power supply to selectively enable and disable first and second flows, respectively, of the electrical power from the power supply between successive pulses of light thereby reducing power consumption;

an amplifier circuit configured to be coupled to the at least one photodetector to receive an electrical signal from the photodetector representative of an amount of light impinging on the photodetector and to amplify that electrical signal, wherein the amplifier circuit is coupled to the first switching circuit to receive at least a portion of the first flow of electrical power; and an LED driver circuit configured to be coupled to the at least one LED to receive an analog electrical signal indicative of a desired light magnitude of the at least one LED and configured to control the current flow through the at least one LED to provide that desired light magnitude, wherein the LED driver circuit is coupled to the second switching circuit to receive at least a portion of the second flow of electrical power.

5. The oximeter of claim 4, further comprising a microcomputer circuit coupled to the first and second switching circuits and configured to signal the first and second switching circuits to enable and disable the first and second flows of electrical power between successive pulses of light from the at least one LED.

6. The oximeter of claim 5, further comprising an analog-to-digital converter circuit coupled to the amplifier circuit to convert the amplified signal to a corresponding digital light value, and further wherein the microcomputer circuit is coupled to the analog-to-digital converter circuit to receive the digital light value and calculate a digital equivalent of an oxygen saturation value based at least upon the digital light value.

7. The oximeter of claim 6, further comprising a digital-to-analog converter circuit coupled to the LED driver circuit to provide the LED driver circuit with the analog electrical signal indicative of a desired light magnitude of the at least one LED, and further wherein the microcomputer circuit is coupled to the digital-to-analog converter circuit to provide the digital-to-analog converter circuit with a digital value indicative of the desired light magnitude.

8. The oximeter of claim 7, wherein the oximeter further comprises an electronic display for displaying the oxygen saturation value.

9. The oximeter of claim 8, wherein the LED driver circuit includes a first operational amplifier, and further wherein the first operational amplifier is coupled to the second switching circuit to receive the at least a portion of the second flow of electrical power.

10. The oximeter of claim 9, wherein the LED driver circuit includes a second operational amplifier, and further wherein the at least one LED includes a first red LED coupled to and driven by the first operational amplifier and a second infrared LED coupled to and driven by the second operational amplifier.

11. A method for reducing the power consumption of a pulse oximeter having a photodetector for detecting pulsatile variations in light transmission through perfused tissue, an amplifier circuit to amplify electrical analogues of the pulsatile variations, an analog-to-digital converter for converting an output of the amplifier circuit into a corresponding digital value, and a microcomputer configured to generate an oxygen saturation based at least upon the digital value, the method comprising the steps of:

(a) generating successive pulses of infrared light;

(b) for each pulse of infrared light, converting at least a portion of the pulse of infrared light into an infrared electrical signal;

(c) connecting the amplifier circuit to a source of electrical power;

(d) amplifying at least a portion of the infrared electrical signal in the amplifier circuit;

(e) transmitting the amplified infrared signal to the analog to digital converter circuit;

(f) disconnecting the amplifier circuit from the source of electrical power after step (e) and between successive pulses of infrared light;

(g) generating successive pulses of red light;

(h) for each pulse of red light, converting at least a portion of the pulse of red light into a red electrical signal;

(i) connecting the amplifier circuit to the source of electrical power after step (g);

(j) amplifying at least a portion of the red electrical signal in the amplifier circuit after step (i);

(k) transmitting the amplified red signal to the analog-to-digital converter; and (l) disconnecting the amplifier circuit from the source of electrical power after step (k) and between successive pulses of light.

12. The method of claim 11, wherein the infrared pulses and the red pulses are generated at least 60 times per second.

13. The method of claim 11, wherein the step of generating successive pulses of infrared light includes the steps of:

converting a digital value indicative of a desired infrared light magnitude into a corresponding analog infrared electrical signal;

applying the analog infrared electrical signal to an LED driver circuit; and regulating a current flow through an infrared LED with the LED driver circuit.

14. The method of claim 13, wherein the step of generating successive pulses of infrared light further includes the steps of:

connecting the LED driver circuit to the source of electrical power prior to the step of regulating a current flow through an infrared LED; and disconnecting the LED driver circuit from the source of electrical power after the pulse of infrared light has been generated.

15. A low-power pulse oximeter, comprising:

a microcomputer configured to generate a digital signal indicative of a desired amount of light;

a digital to analog converter circuit coupled to the microcomputer to convert the digital signal into an analog signal indicative of a desired amount of light;

at least one source amplifier circuit coupled to the digital to analog converter circuit to amplify the analog signal to an amplitude sufficient to generate the desired amount of light;

a power supply coupled to the at least one source amplifier circuit to provide power to the at least one LED amplifier/driver circuit;

a light source coupled to the at least one source amplifier circuit and configured to generate the desired amount of light in the form of successive pulses at predetermined intervals upon receipt of the amplified analog signal; and a switching circuit electrically interposed between the power supply and the at least one source amplifier circuit to selectively interrupt a flow of electrical power from the power supply to the at least one source amplifier circuit between the successive pulses.

16. The low-power pulse oximeter of claim 15, wherein the source amplifier circuit includes a first operational amplifier, and further wherein the light source includes a first LED, and further wherein the digital signal indicative of a desired amount of light includes a first digital signal indicative of a desired amount of red light, and further wherein the first operational amplifier is coupled to the first LED to control a current flow through the first LED in response to the first digital signal indicative of a desired amount of red light.

17. The low-power pulse oximeter of claim 16, wherein the source amplifier circuit includes a second operational amplifier, and further wherein the light source includes a second LED, and further wherein the digital signal indicative of a desired amount of light includes a second digital signal indicative of a desired amount of infrared light, and further wherein the second operational amplifier is coupled to the second LED to control a current flow through the second LED in response to the second digital signal indicative of a desired amount of infrared light.

18. A medical monitoring system, comprising:

a sensor configured to sense a physical parameter of a patient and to generate a sensor signal;

at least one amplifier that is coupled to the sensor to amplify the sensor signal;

a battery that is coupled to the at least one amplifier to provide power to the at least one amplifier;

an analog to digital converter that is coupled to the amplifier to receive and convert the amplified signal to a digital signal;

a microcomputer circuit configured to receive the digital signal and to calculate a value indicative of the physical parameter therefrom; and a switching circuit disposed between the at least one amplifier and the battery, wherein the microcomputer circuit is coupled to the switching circuit and is configured to signal the switching circuit to selectively interrupt a flow of electrical power from the battery to the at least one amplifier between successive digital signal conversions;

wherein the sensor continues to generate a sensor signal at predetermined intervals when the switching circuit interrupts the flow.

19. The medical monitoring system of claim 18, wherein the battery is coupled to the microcomputer circuit to provide power to the microcomputer circuit.

20. The medical monitoring system of claim 19, further comprising an enclosure, and further wherein the enclosure encloses the microcomputer circuit and the battery.

21. The medical monitoring system of claim 20, wherein the microcomputer circuit is configured to retrieve a sensor value from the analog to digital converter, then turn the power to the amplifier off, then to wait a predetermined period of time, and then to turn the power to the amplifier circuit on.

22. The medical monitoring system of claim 21, wherein the microcomputer circuit is configured to turn the amplifier circuit off and on by controlling the switching circuit.

* * * * *